(12) United States Patent
Collins

(10) Patent No.: US 10,383,710 B2
(45) Date of Patent: Aug. 20, 2019

(54) CONFIGURATIONS FOR THE CONNECTION OF DENTAL RESTORATIONS WITH ABUTMENTS

(71) Applicant: Zimmer, Inc., Warsaw, IN (US)

(72) Inventor: Michael Scott Collins, San Marcos, CA (US)

(73) Assignee: Zimmer, Inc., Warsaw, IN (US)

( * ) Notice: Subject to any disclaimer, the term of this patent is extended or adjusted under 35 U.S.C. 154(b) by 75 days.

(21) Appl. No.: 15/002,622

(22) Filed: Jan. 21, 2016

(65) Prior Publication Data

US 2016/0228220 A1    Aug. 11, 2016

Related U.S. Application Data

(60) Provisional application No. 62/114,116, filed on Feb. 10, 2015.

(51) Int. Cl.
 *A61C 8/00* (2006.01)
 *A61C 13/265* (2006.01)

(52) U.S. Cl.
 CPC ............ *A61C 8/0095* (2013.01); *A61C 8/005* (2013.01); *A61C 8/0012* (2013.01); *A61C 8/0037* (2013.01); *A61C 8/0048* (2013.01); *A61C 8/0074* (2013.01); *A61C 13/2656* (2013.01); *A61C 2008/0046* (2013.01)

(58) Field of Classification Search
 CPC ... A61C 8/0095; A61C 8/0012; A61C 8/0037; A61C 8/0048; A61C 8/005; A61C 8/0074; A61C 8/0093; A61C 13/2656; A61C 2008/0046

USPC ............... 433/2.26, 2.29, 167–176
See application file for complete search history.

(56) References Cited

U.S. PATENT DOCUMENTS

| | | | | |
|---|---|---|---|---|
| 4,568,285 A | * | 2/1986 | Chiaramonte | A61C 8/0018 433/169 |
| 4,881,897 A | * | 11/1989 | Franek | A61C 8/0018 433/169 |
| 4,932,868 A | * | 6/1990 | Linkow | A61C 8/0018 433/174 |
| 4,993,950 A | * | 2/1991 | Mensor, Jr. | A61C 8/0048 433/173 |
| 5,282,861 A | | 2/1994 | Kaplan | |
| 5,520,540 A | * | 5/1996 | Nardi | A61C 8/0048 433/172 |
| 5,564,922 A | * | 10/1996 | Rosa | A61C 8/005 433/173 |
| 9,055,993 B2 | * | 6/2015 | Grobbee | A61C 13/2656 |
| 9,456,881 B1 | * | 10/2016 | Niznick | A61C 8/0053 |
| 2006/0024644 A1 | * | 2/2006 | Cohen | A61C 8/005 433/173 |

(Continued)

OTHER PUBLICATIONS

U.S. Appl. No. 62/000,772. Robichaud, Jean. "Attachment System for Removable Dental Prosthesis and Dental Implant Abutment." filed May 20, 2014. USPTO.*

*Primary Examiner* — Yogesh P Patel

(74) *Attorney, Agent, or Firm* — Schwegman Lundberg & Woessner, P.A.

(57) ABSTRACT

Dental prostheses are disclosed including a dental prosthesis that can comprise an abutment and a component stabilized with vitamin E. The abutment can be adapted to be secured in a patient's jaw. The component can be adapted to couple the abutment to a dental appliance.

25 Claims, 8 Drawing Sheets

(56) References Cited

U.S. PATENT DOCUMENTS

| | | | |
|---|---|---|---|
| 2007/0020582 A1* | 1/2007 | Neumeyer | A61C 8/005 433/173 |
| 2008/0153063 A1* | 6/2008 | Mullaly | A61C 8/0018 433/174 |
| 2008/0261174 A1* | 10/2008 | Gittleman | A61C 8/0048 433/172 |
| 2009/0011384 A1* | 1/2009 | Collins | A61C 8/0012 433/174 |
| 2009/0192610 A1* | 7/2009 | Case | A61F 2/34 623/16.11 |
| 2009/0317769 A1* | 12/2009 | Urdaneta | A61C 8/005 433/202.1 |
| 2009/0325125 A1* | 12/2009 | Diangelo | A61C 8/0001 433/173 |
| 2010/0055645 A1* | 3/2010 | Mullaly | A61C 8/0025 433/174 |
| 2010/0112520 A1* | 5/2010 | Worthington | A61C 8/0001 433/169 |
| 2010/0183998 A1* | 7/2010 | Poirier | A61C 8/0048 433/72 |
| 2011/0014587 A1* | 1/2011 | Spagnoli | A61C 8/0006 433/174 |
| 2011/0195379 A1* | 8/2011 | Allaire | A61C 8/0048 433/174 |
| 2012/0046752 A1* | 2/2012 | Blanchard | A61F 2/30756 623/18.11 |
| 2012/0141955 A1* | 6/2012 | Kim | A61C 8/0013 433/174 |
| 2012/0214128 A1* | 8/2012 | Collins | A61C 8/0012 433/173 |
| 2013/0209958 A1* | 8/2013 | Benz | A61C 8/005 433/173 |
| 2013/0323679 A1* | 12/2013 | Berger | A61C 13/0001 433/173 |
| 2014/0106303 A1* | 4/2014 | Giasson | A61C 8/0048 433/173 |
| 2014/0134571 A1* | 5/2014 | Lemke | A61C 8/0095 433/174 |
| 2014/0162212 A1* | 6/2014 | Mullaly | A61C 8/0053 433/173 |
| 2014/0178839 A1* | 6/2014 | Berger | A61C 13/2255 433/173 |
| 2014/0272383 A1* | 9/2014 | Muratoglu | A61L 31/048 428/319.9 |
| 2014/0272792 A1* | 9/2014 | Haralampopoulos | A61C 8/0068 433/173 |
| 2015/0250569 A1* | 9/2015 | Frick | A61C 8/005 433/202.1 |
| 2015/0335401 A1* | 11/2015 | Robichaud | A61C 8/0063 433/173 |
| 2016/0287395 A1* | 10/2016 | Khalili | A61F 2/30942 |
| 2017/0105843 A1* | 4/2017 | Britton | A61F 2/4081 |

* cited by examiner

CONFIGURATIONS FOR THE CONNECTION OF DENTAL RESTORATIONS WITH ABUTMENTS

CLAIM OF PRIORITY

This application claims the benefit of U.S. Provisional Patent Application Ser. No. 62/114,116, filed on Feb. 10, 2015, the benefit of priority of which is claimed hereby, and which is incorporated by reference herein in its entirety.

TECHNICAL FIELD

The present patent application relates to dental restorations, and more particularly, to configurations for the connection of dental restorations with abutments.

BACKGROUND

Conventional dentures have prosthetic teeth shaped and colored to appear like natural teeth. The base of the denture is colored to match gingival or soft tissue, and is fixed upon a patient's gingiva by an adhesive. However, the denture may not adhere well to the patent's gum causing discomfort and malfunction of the denture as well as embarrassment to the patient when the denture slips out of the patient's mouth.

As such, endosseous implants may be used to anchor the denture to support multiple prosthetic teeth. The denture fits over implants, or shortened natural teeth if preserved, and is called an overdenture. The overdenture can also be used in cases where the mandible or maxilla of a patient has insufficient bone mass or strength to hold an implant for each tooth, or when a surgery for many implants is cost prohibitive or otherwise harmful to the patient Endosseous dental implants are typically threaded or press-fit into pre-drilled bores in the mandible or maxilla to support one or more prosthetic teeth. A number of implants can be spaced along the mandible or maxillae and may be used to support a full or partial overdenture. A full denture with prosthetic teeth for an entire upper or lower jaw is usually anchored by two to four implants.

OVERVIEW

The present inventor has recognized that attachments (e.g., abutments used for coupling dental appliances (e.g., crowns, dentures, and other dental restorations) can be subject to occlusal, shock, and other forces during use. These forces can lead to excessive wear, and in some instances, bone loss and/or patient discomfort. Additionally, the replacement and maintenance of conventional attachment systems can require time consuming and costly procedure including repair and/or removal and replacement at recall appointments. In view of the forgoing, the present application discloses a dental prosthesis that can comprise an abutment and a component stabilized with vitamin E. The abutment can be adapted to be secured in a patient's jaw. The component can be adapted to couple the abutment to a dental appliance. In some examples, the component can comprise one of a cap, a spacer, or an insert. According to one example, the component can comprise the insert, which can be adapted to be disposed in a recess of the dental appliance and can be configured to interface with the abutment and at least a second abutment. According to another example, the component can comprise the cap, which can be adapted to be disposed in a recess of the dental appliance and can have a portion adapted to interface with and act as an articulation surface with the abutment. In yet another example, the insert can comprise the spacer, which can be configured to couple to a metal cap that is adapted to insert in a recess of the dental appliance. In further examples, the component can comprise a material such as an ultra-high molecular weight polyethylene and vitamin E.

To better illustrate the prostheses disclosed herein, a non-limiting list of examples is provided here:

In Example 1, a dental prosthesis can comprise an abutment adapted to be secured in a patient's jaw and a component stabilized with vitamin E and adapted to couple the abutment to a dental appliance.

In Example 2, the prosthesis of Example 1 wherein the component can comprise one of a cap, a coping, a spacer, or an insert.

In Example 3, the prosthesis of Example 1, wherein the component can comprise an insert, and wherein the insert can be adapted to be disposed in a recess of the dental appliance and can be configured to interface with the abutment and at least a second abutment.

In Example 4, the prosthesis of Example 1, wherein the component can comprise a cap, and wherein the cap can be adapted to be disposed in a recess of the dental appliance and can have a portion adapted to interface with and act as an articulation surface with the abutment.

In Example 5, the prosthesis of Example 1, wherein the component can comprise a spacer, and wherein the spacer can be configured to couple to a metal cap that can be adapted to insert in a recess of the dental appliance.

In Example 6, the prosthesis of any one or any combination of Examples 1 to 5, wherein the abutment can include at least one of the following coupling mechanisms: a male connection structure, a female connection structure, a ball, a spherical socket, a locator arrangement, and an integral bar forming a single-piece with the abutment.

In Example 7, the prosthesis of any one or any combination of Examples 1 to 6, wherein a proximal end portion of the abutment can be configured to snap-fit to the component.

In Example 8, the prosthesis of any one or any combination of Examples 1 to 5, can further comprise a bar configured to extend along the patent's jaw, the bar can be adapted to couple with the abutment and to secure the abutment to one or more additional abutments.

In Example 9, the prosthesis of any one or any combination of Examples 1 to 8, can further comprise a dental implant that can be configured to couple with the abutment and adapted for implantation in the patient's jaw.

In Example 10, the prosthesis of Example 9, wherein the dental implant can have a porous metal portion of tantalum or niobium adapted to interface with a bone of the patent's jaw.

In Example 11, the prosthesis of any one or any combination of Examples 1 to 10, wherein the dental appliance can comprise an overdenture and the component can comprise ultra-high molecular weight polyethylene and vitamin E.

In Example 12, a dental prosthesis can comprise an abutment, a dental implant configured to couple to the abutment and adapted to implant in the patient's jaw, and at least one of a cap or coping. The cap or coping can comprise an ultra-high molecular weight polyethylene and vitamin E, wherein the cap or coping can be adapted to couple with the dental appliance and can have a portion adapted to interface with and act as an articulation surface for the abutment.

In Example 13, the prosthesis of Example 12, wherein a proximal end portion of the abutment can be configured to snap-fit to the cap or coping.

In Example 14, a dental prosthesis can comprise a plurality of abutments, a bar, a plurality of spacers, and a plurality of metal caps. The bar can be adapted to couple with the plurality of abutments and secure the plurality of abutments together, the bar configured to extend along a patent's jaw. The plurality of spacers can each comprise ultra-high molecular weight polyethylene and vitamin E, each spacer can be configured to couple to one of the plurality of abutments. The plurality of metal caps can each be adapted to couple with a dental appliance and can each be configured to couple with one of the plurality of spacers.

In Example 15, the prosthesis of Example 14, wherein a proximal end portion of each spacer can be configured to snap-fit to one of the plurality of metal caps.

In Example 16, the prosthesis of one or any combination of Examples 14 to 15, wherein the plurality of abutments can be integral with the bar.

In Example 17, a dental prosthesis can comprise a plurality of abutments, a bar, and an insert. The bar can be adapted to couple with the plurality of abutments and can secure the plurality of abutments together, the bar can be configured to extend along a patent's jaw. The insert can comprise an ultra-high molecular weight polyethylene and vitamin E and can be adapted to couple with a dental appliance and configured to couple with the plurality of abutments.

In Example 18, the prosthesis of Example 17, wherein a proximal end portion of each abutment can be configured to snap-fit to the insert.

In Example 19, the prosthesis of one or any combination of Examples 17 to 18, wherein the plurality of abutments can be integral with the bar.

In Example 20, the apparatus or system of any one or any combination of Examples 1-19 can optionally be configured such that all elements or options recited are available to use or select from.

These and other examples and features of the present prostheses will be set forth in part in the following Detailed Description. This overview is intended to provide a summary of subject matter of the present patent application. It is not intended to provide an exclusive or exhaustive recitation of the invention. The detailed description is included to provide further information about the present patent application.

BRIEF DESCRIPTION OF PIE DRAWINGS in the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to dental restorations, and in one example, to a dental prosthesis that can comprise an abutment and a component stabilized with vitamin E. For example, the component can comprise a material such as an ultra-high molecular weight polyethylene and vitamin E. The component stabilized with vitamin E provides an increased ability to absorb occlusal, shock, and other forces that can occur during use. Thus, the disclosed dental prostheses can reduce the likelihood of excessive wear, bone loss, and/or patient discomfort. Additionally, the disclosed dental prostheses can reduce the likelihood of replacement and/or maintenance, thereby reducing the cost and time associated with follow-up appointments.

Figure 1:
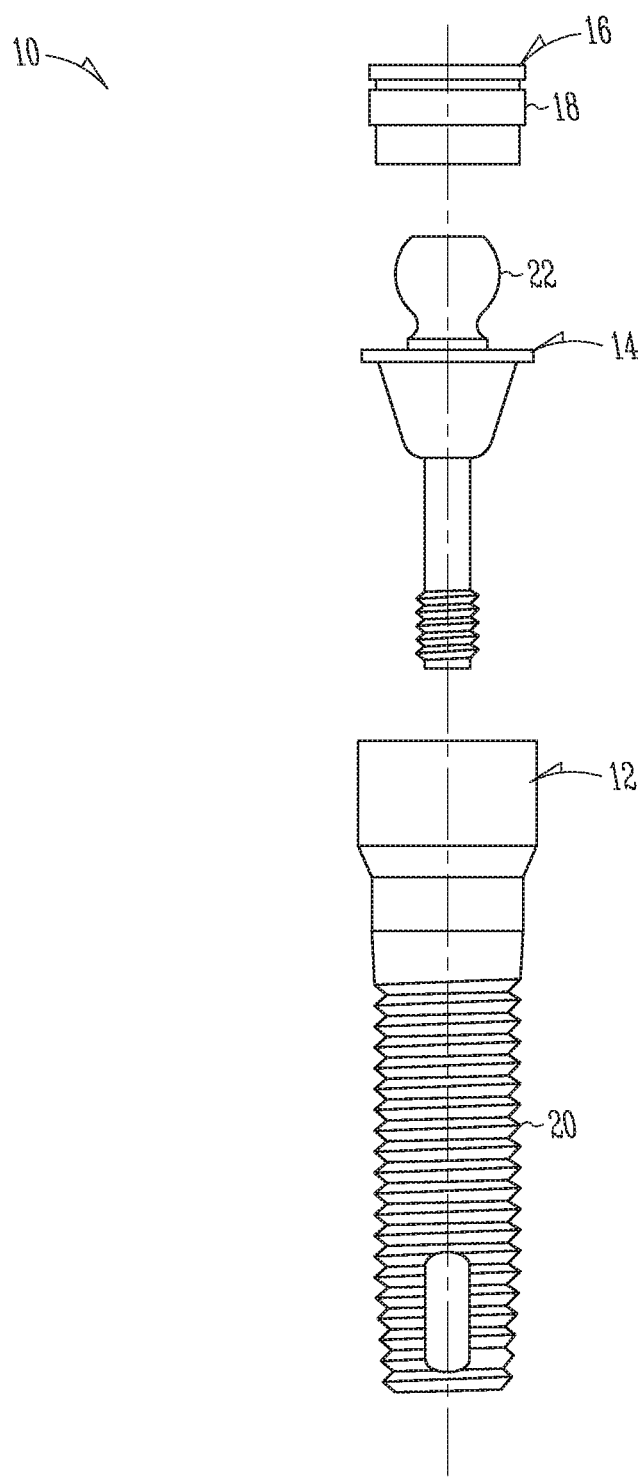
FIG. 1 is an exploded view showing a dental prosthesis including a dental implant, an abutment and a component comprising a cap according to an example of the present disclosure.

FIG. 1 shows a dental prosthesis 10 according to an example of the present disclosure. The dental prosthesis 10 can include a dental implant 12, an abutment 14, and a component 16. According to the example of FIG. 1, the component 16 comprises a cap 18.

As shown in FIG. 1, the dental implant 12 can be configured to couple with the abutment 14. For example, the dental implant 12 can include a threaded portion adapted to secure to a threaded portion of the abutment 14 as shown in FIG. 1. In other examples, the abutment 14 and dental implant 12 can be otherwise coupled together, for example, they can be integral with one another so that the abutment 14 and the dental implant 12 comprise a single-piece component. As used herein, the term abutment can include a variety of dental prosthesis components including dental implants having integral abutments, and components adapted to couple with or that are otherwise associated with an abutment including intermediate abutments, attachments (e.g., balls, caps, copings, couplings, linkages, etc.), bars, etc. For example, traditional Zirconia material that acts as a cap/coping over a metal abutment base can be replaced with vitamin E. Thus, according to some examples an abutment could comprise the aforementioned base, as well as the cap/coupling.

Figure 2A:
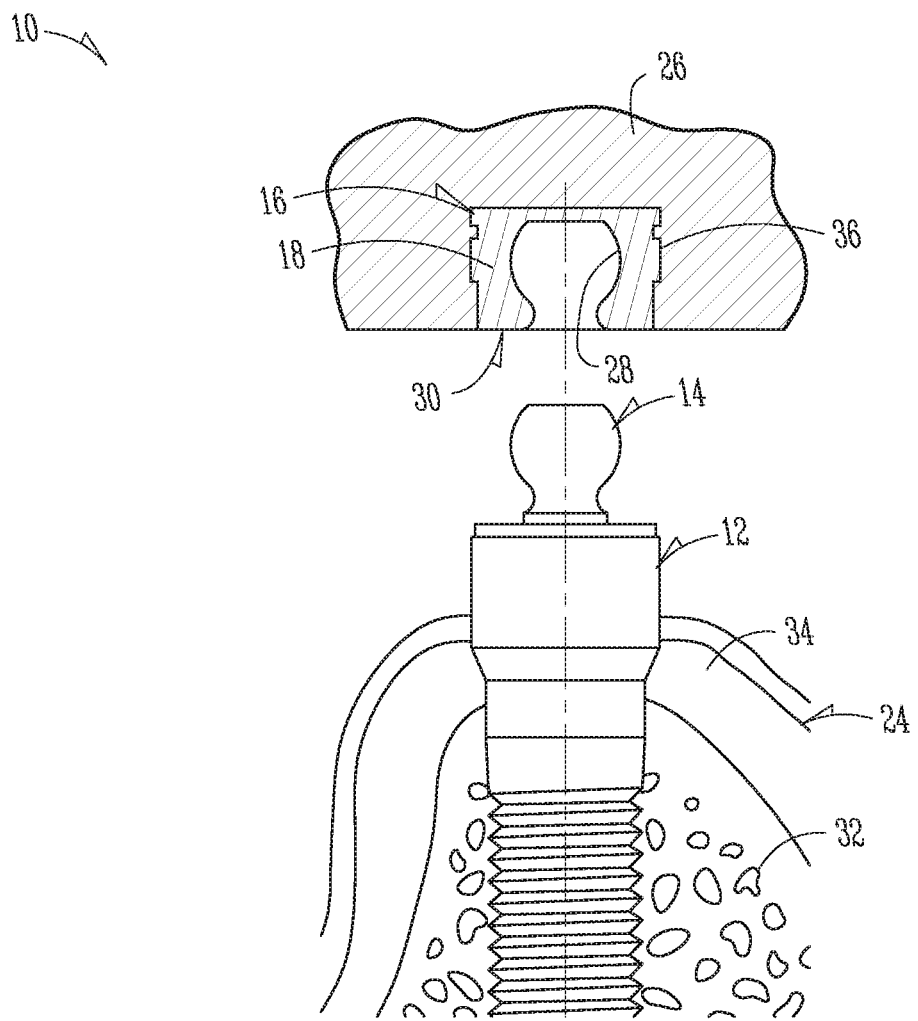
FIG. 2A is a view of the dental prosthesis of FIG. 1 with the dental implant inserted in a patient's jaw and the cap inserted in a dental appliance according to an example of the present disclosure.
Figure 2B:
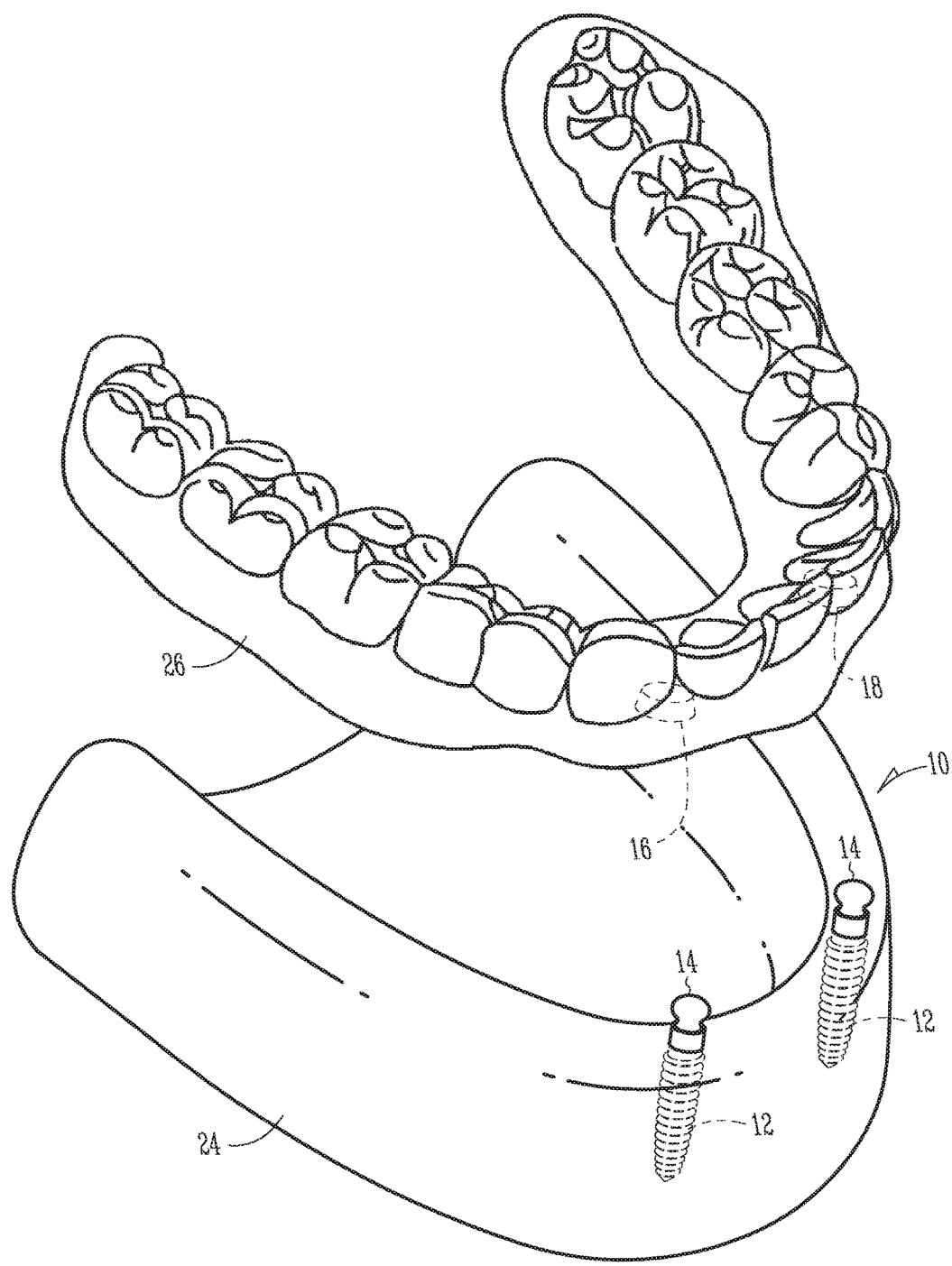
FIG. 2B is a perspective view of two dental prostheses such as those of FIGS. 1 and 2A arranged in the patient's jaw and in the dental appliance according to an example of the present disclosure.

As illustrated in FIG. 1, the dental implant 12 can be adapted to implant in the patient's jaw (see also FIGS. 2A and 2B). For example, the dental implant 12 can be provided with an external threaded portion 20 that is adapted to thread with bone in a tapped cavity within the patient's jaw. According to further examples, the dental implant 12 can include a porous metal portion of tantalum and/or niobium adapted to interface with a bone of the patent's jaw. Such a porous metal portion can be produced using Trabecular Metal™ technology generally available from Zimmer, Inc.

of Warsaw, Ind. Such material can be formed from a reticulated vitreous carbon foam substrate which is infiltrated and coated with a biocompatible metal, such as tantalum, etc., by a chemical vapor deposition ("CVD") process in a manner disclosed in detail in U.S. Pat. No. 5,282,861, the disclosure of which is fully incorporated herein by reference. Other metals such as niobium, alloys of tantalum and niobium, or alloys with other metals can also be used. The porous metal portion may include up to 75%-85% or more voids therein and closely resembles the structure of natural cancellous bone, thereby providing a matrix into which cancellous bone may grow to anchor implant into the surrounding bone of a patients jaw which increases implant stability.

As illustrated in FIG. 1, the abutment 14 can be configured to couple with the component 16. For example, the abutment 14 can include a ball or sphere on a proximal end portion 22 that is adapted to mate or otherwise couple with a corresponding feature in the component 16. According to the example of FIG. 1, the proximal end portion 22 of the abutment 14 can be configured to snap-fit to the component 16. Although a ball coupling mechanism is illustrated in FIG. 1, further examples can provide for various coupling mechanisms known to one of ordinary skill in the art. For example, the abutment 14 can include coupling mechanisms such as a male connection structure, a female connection structure, a spherical socket, a locator structure, a collar, a cap, and an integral bar forming a single-piece with the abutment, etc. Further examples of abutment configurations that are compatible with the vitamin E stabilized components disclosed herein include, for example, the Locator®, which is produced by Zest Anchors of Escondido, Calif., and Zimmer® Contour Zirconia Abutments, which are produced by Zimmer Dental Inc., a division of Zimmer Inc. of Warsaw, Ind.

According to the example of FIG. 1, the component 16 can be vitamin E stabilized and can be comprised of a material such as an ultra-high molecular weight polyethylene and vitamin E. Such ultra-high molecular weight polyethylene and vitamin E combination can comprise, for example, Vivacit-E® Vitamin E Highly Crosslinked Polyethylene, which is manufactured by Zimmer Inc. of Warsaw, Ind. Thus, according to some examples, the vitamin E of the component 16 can have a concentration between about 0.01 to about 0.16 weight percent. The component 16 stabilized with vitamin E can provide an increased ability to absorb occlusal, shock, and other forces that can occur during use. Thus, the disclosed dental prosthesis 10 can reduce the likelihood of excessive wear on the dental prosthesis and the dental appliance and can reduce the likelihood of patient bone loss and/or patient discomfort.

FIGS. 2A and 2B further illustrate the dental prosthesis 10 disposed in a patient's jaw 24 and in a dental appliance 26 such as a denture. FIG. 2A illustrates the jaw 24, the dental appliance 26, and the cap 18 in cross-section. FIG. 2B illustrates the dental appliance 26 removed from the jaw 24 and a portion of the dental prosthesis 10 that anchors in the jaw 24.

As illustrated in FIGS. 2A and 2B, the component 16 can be adapted to couple the abutment 14 to the dental appliance 26. Similar to FIG. 1, FIGS. 2A and 2B provide an example where the component 16 comprises the cap 18. The cap 18 can be adapted to be disposed in a recess 30 (FIG. 2A) of the dental appliance 26 and has a coupling portion 28 adapted to interface with and act as an articulation surface with the abutment 14. As discussed, the coupling portion 28 (FIG. 2A) can be configured to snap-fit the component 16 with the proximal end portion of the abutment 14 to couple the abutment 14 with the component 16. In FIG. 2A, the coupling portion 28 (FIG. 2A) comprises a spherical socket adapted to receive the ball of the abutment 14 therein. However, other coupling configurations such as a male connection structure, a female connection structure, locator, etc. can be utilized as desired.

FIG. 2A illustrates the dental prosthesis 10 can have the dental implant 12 disposed in bone 32 of the jaw 24. As shown in FIG. 2A, the dental prosthesis 10 extends from the bone 32 and a gum 34 and is coupled to the abutment 14. In addition to the coupling portion 28, the cap 18 can have an outer portion 36 adapted to be received in the recess 30 (FIG. 2A) of the dental appliance 26 by snap-fit or other suitable connection (e.g., thread, biocompatible adhesive, locking mechanism, etc.).

FIG. 2B illustrates that the dental prosthesis 10 can comprise a plurality of prostheses (e.g. two to four or more). FIG. 2B also illustrates that each component 16 (e.g., caps 18) can be configured to be disposed in the dental appliance 26 while the remainder of the dental prosthesis (e.g., the abutment 14 and the dental implant 12) can couple to the jaw 24. The dental prostheses 10 can he adapted to connect the dental appliance 26 to the jaw 24. More particularly, the dental appliance 26 can be adapted to overlay the jaw 24 such that each abutment 14 can interface with the corresponding cap 18. The dental appliance 26 can be coupled to the jaw 24 by coupling each abutment 14 to the corresponding cap 18 by, for example, snap-fit or other suitable connection.

Figure 3:
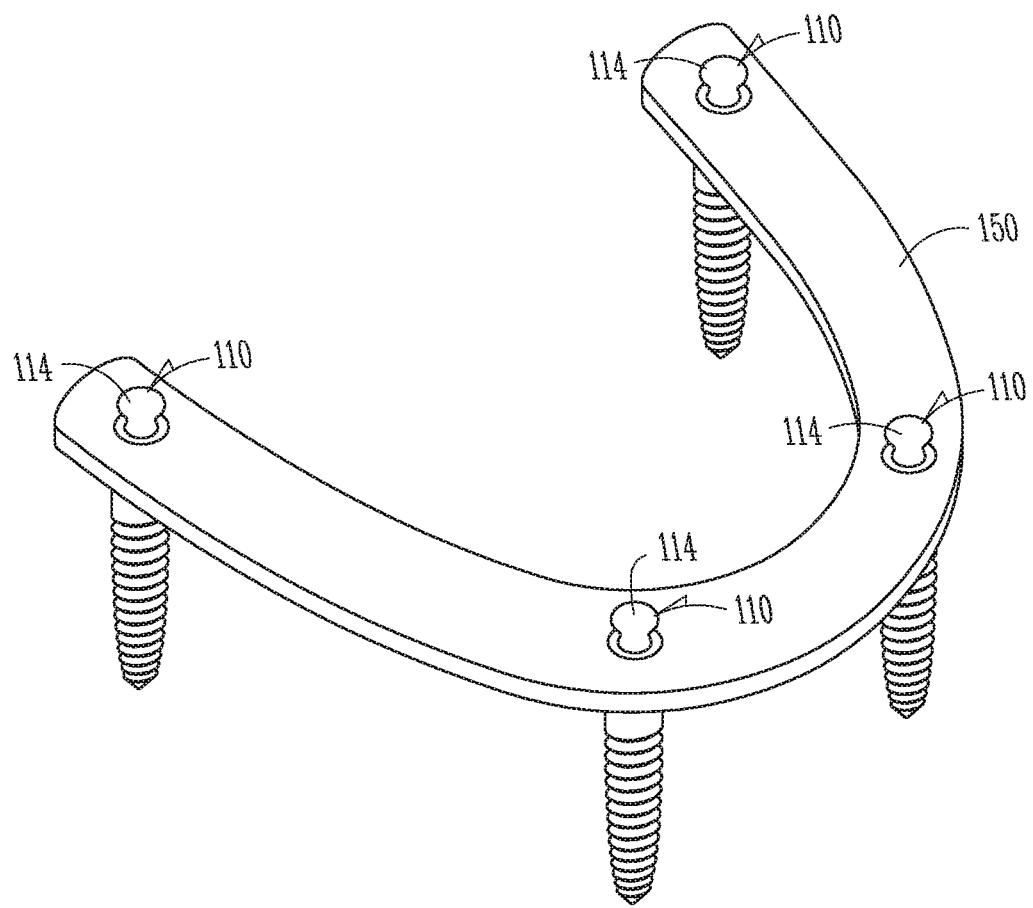
FIG. 3 is a perspective view of a bar coupled with a plurality of abutments according to an example of the present disclosure.

FIG. 3 shows a plurality of dental prostheses 110 can be connected to a bar 150. The bar 150 can be configured to extend along the arch of the patent's jaw. As illustrated, the bar 150 can be adapted to couple with each abutment 114 and secure the abutments 114 together.

Indeed, the bar 150 can comprise a curved attachment that can be used to connect two or more dental prostheses 110 to a rigid frame for a full denture, overdenture or partial denture. The bar 150 can be constructed in a number of different sizes and manners to accommodate varying patients' dental arch, and can be made of suitably strong material such as titanium, titanium alloys, cobalt-chromium alloys, cobalt-chromium-molybdenum alloys, stainless steel with a titanium nitride coating, zirconium, etc. According to some examples, the bar 150 may also be cut into partial arch shapes that are straight and/or curved of various lengths. In FIG. 3, the bar 150 is illustrated as coupling with the dental prostheses 110 via a bore and collar or similar mechanism. However, in other examples the bar 150 and abutment 114 can be integrally formed as a single-piece, threaded together, snap-fitted together, etc. as desired. Similarly, according to some examples, the dental prosthesis can include an abutment that is separate from the dental implant. Thus, the dental implant can be coupled to the bar separate from the abutment. For example, the abutment can be attached to the bar at a first lateral location along the bar and the dental implant can be coupled to the bar at a different lateral location along the bar.

Figure 4:
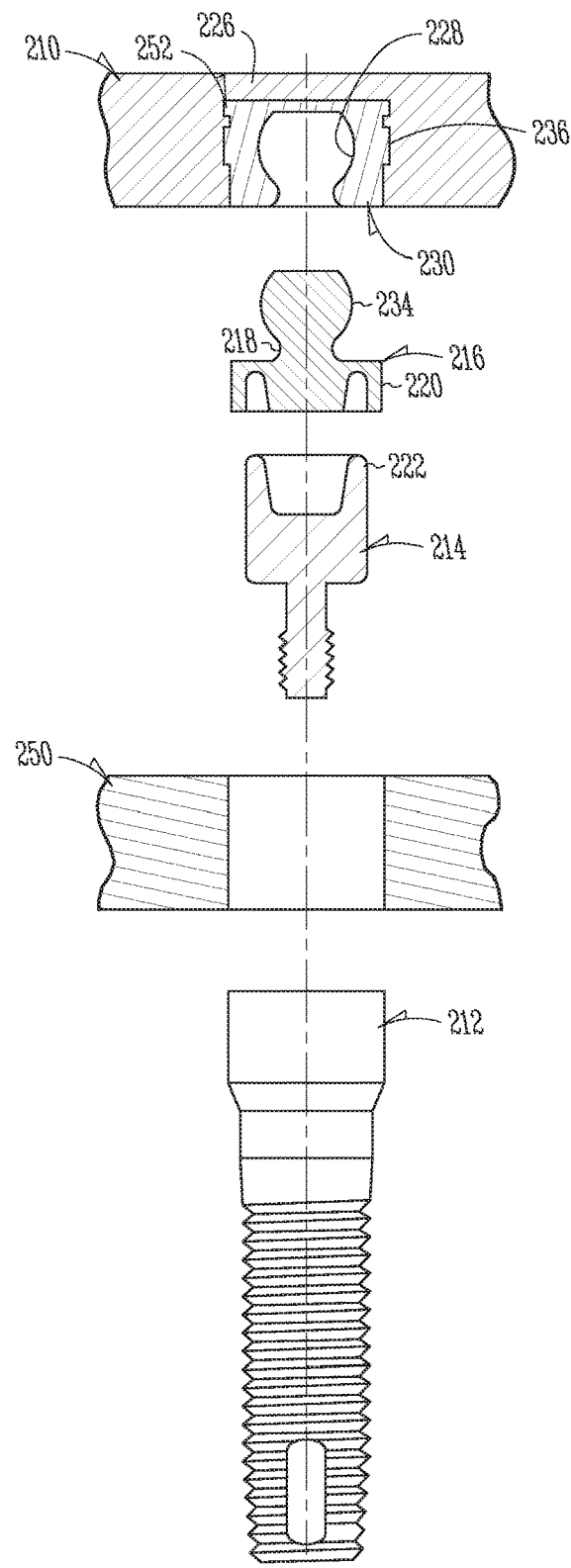
FIG. 4 is an exploded view of a dental prosthesis including an abutment and a component comprising a spacer according to an example of the present disclosure.
Figure 5:
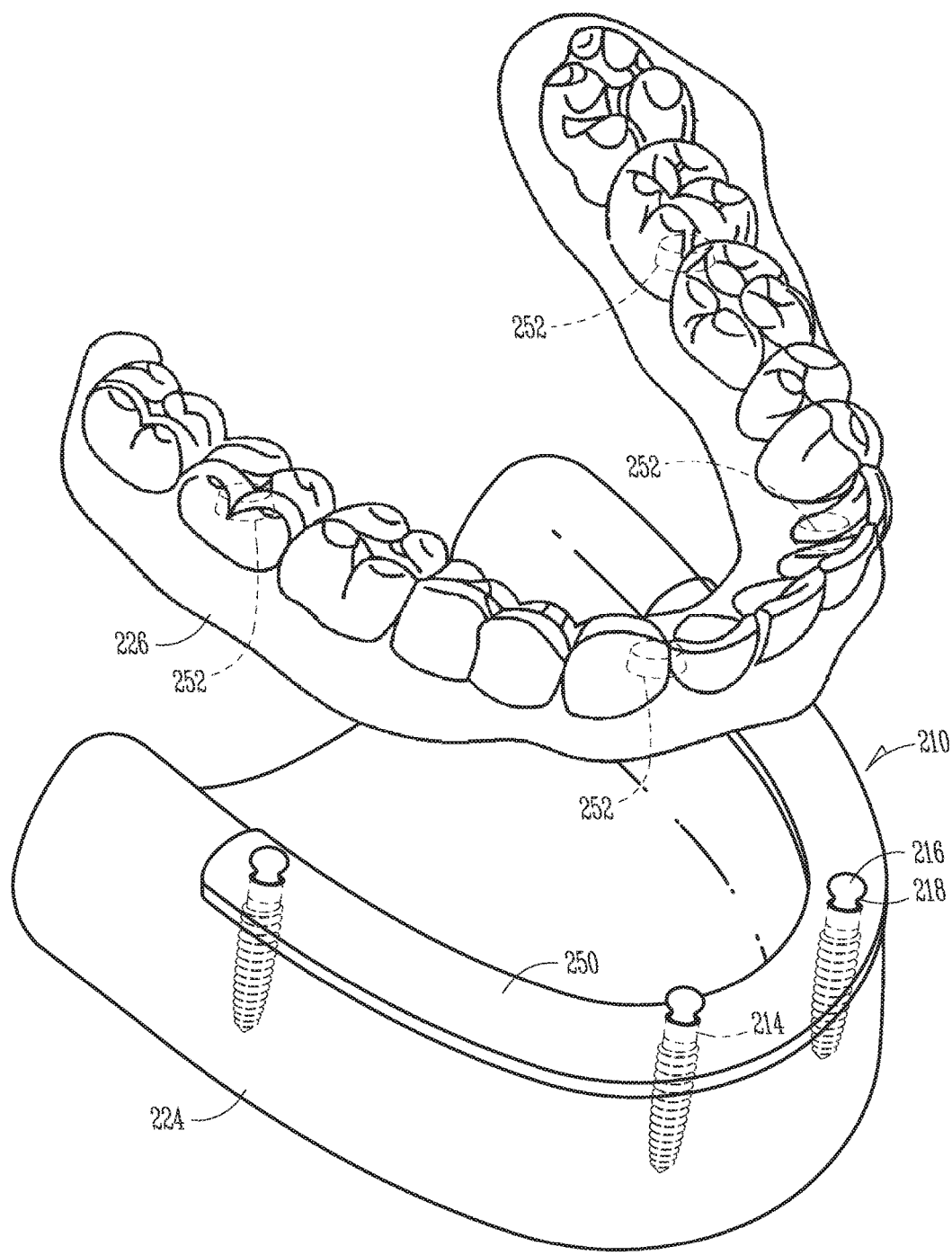
FIG. 5 is a perspective view of a plurality of dental prostheses such as those of FIG. 4 arranged in the patient's jaw and in a dental appliance according to an example of the present disclosure.

FIGS. 4 and 5 show a dental prosthesis 210 according to an example of the present disclosure. The dental prosthesis 210 can include a dental implant 212, an abutment 214, a component 216, a bar 250, and a cap 252. According to the example of FIGS. 4 and 5, the component 216 can comprise a spacer 218.

In FIG. 4, the dental implant 212 can be configured to couple with the abutment 214. As previously discussed, this can be accomplished by snap-fit, threads, collars, interlocking features, integrally forming the dental implant 212 with the abutment 214, etc. According to the example of FIG. 4, the dental implant 212 and abutment 214 can he designed to couple together through an intermediate component such as the bar 250. Only a portion of bar 250 is illustrated in FIG. 4, however, the construction of the bar 250 can be similar to that of the bar 150 of FIG. 3.

FIG. 4 illustrates the abutment 214 can include a proximal end portion 222 configured as a female type connection having a rim and central recess. The component 216 (e.g., the spacer 218) can be configured to couple to the abutment 214 at a distal end portion 220 thereof. In the example of FIG. 4, the distal end portion 220 can be configured as a locator element to attach to the correspondingly shaped rim and central recess of the proximal end portion 222 of the abutment 214. According to some examples, the coupling arrangement can snap-fit the proximal end portion 222 of the abutment 214 to the component 216 (e.g., the spacer 218) to couple the abutment 214 with the component 216.

A proximal end portion 234 of the component 216 can be configured to couple with the cap 252. In the example of FIG. 4, the proximal end portion 234 is configured as a ball and the cap 252 can have a coupling portion 228 that comprises a spherical socket adapted to receive the ball of the component 216 therein. However, other coupling configurations such as a male connection structure, a female connection structure, locator, etc. can be utilized as desired, According to some examples, the coupling arrangement can snap-fit the component 216 (e.g., the spacer 218) to the coupling portion 228 of the cap 252 to couple the component 216 with the cap 252. The cap 252 can have an outer portion 236 adapted to be received in a recess 230 of the dental appliance 226 by snap-fit or other methods (e.g., thread, biocompatible adhesive, locking mechanism, etc.). According to one example, the cap 252 can be made of suitably strong material such as titanium, titanium alloys, cobalt-chromium alloys, cobalt-chromium-molybdenum alloys, stainless steel with a titanium nitride coating, zirconium, etc.

According to the example of FIG. 4, the component 216 can be vitamin E stabilized and can be comprised of a material such as an ultra-high molecular weight polyethylene and vitamin E as described previously with regard to the examples of FIGS. 1, 2A, and 2B. The component 216 stabilized with vitamin E provides an increased ability to absorb occlusal, shock, and other forces that can occur during use. Thus, the disclosed dental prosthesis 210 can reduce the likelihood of excessive wear on the dental prosthesis and the dental appliance and can reduce the likelihood of patient bone loss and/or patient discomfort.

FIG. 5 illustrates that the dental prosthesis 210 can comprise a plurality of prostheses (e.g. two to four or more). FIG. 5 illustrates that the component 216 (e.g., spacer 218) can be configured to couple to the cap 252 disposed in the dental appliance 226 while the remainder of the dental prosthesis (e.g., the abutment 214, the dental implant (not shown), and the bar 250) can couple to the jaw 224. The dental prosthesis 210 can be adapted to connect the dental appliance 226 to the jaw 224. More particularly, the dental appliance 226 is adapted to overlay the jaw 224 such that each abutment 214/spacer 218 can interface with a corresponding cap 252. The dental appliance 226 can be coupled to jaw 224 by coupling each spacer 218 to the corresponding cap 252 by, for example, snap-fitting the corresponding spacer 218 and the cap 252 together.

According to one example, the dental prosthesis 210 can comprise the plurality of abutments 214, the bar 250, the plurality of spacers 218, and the plurality of metal caps 252. The bar 250 can be adapted to couple with the plurality of abutments 214 and can secure the plurality of abutments 214 together. The bar 250 can be configured to extend along a patent's jaw (e.g., along an arch on the mandible or maxilla). The plurality of spacers 218 can each comprise an ultra-high molecular weight polyethylene and vitamin E. Each spacer 218 can be configured to couple to one of the plurality of abutments 214. Each cap 252 can be adapted to insert in a recess of the dental appliance 226 and each cap 252 can be configured to couple with one of the plurality of spacers 218.

Figure 6:
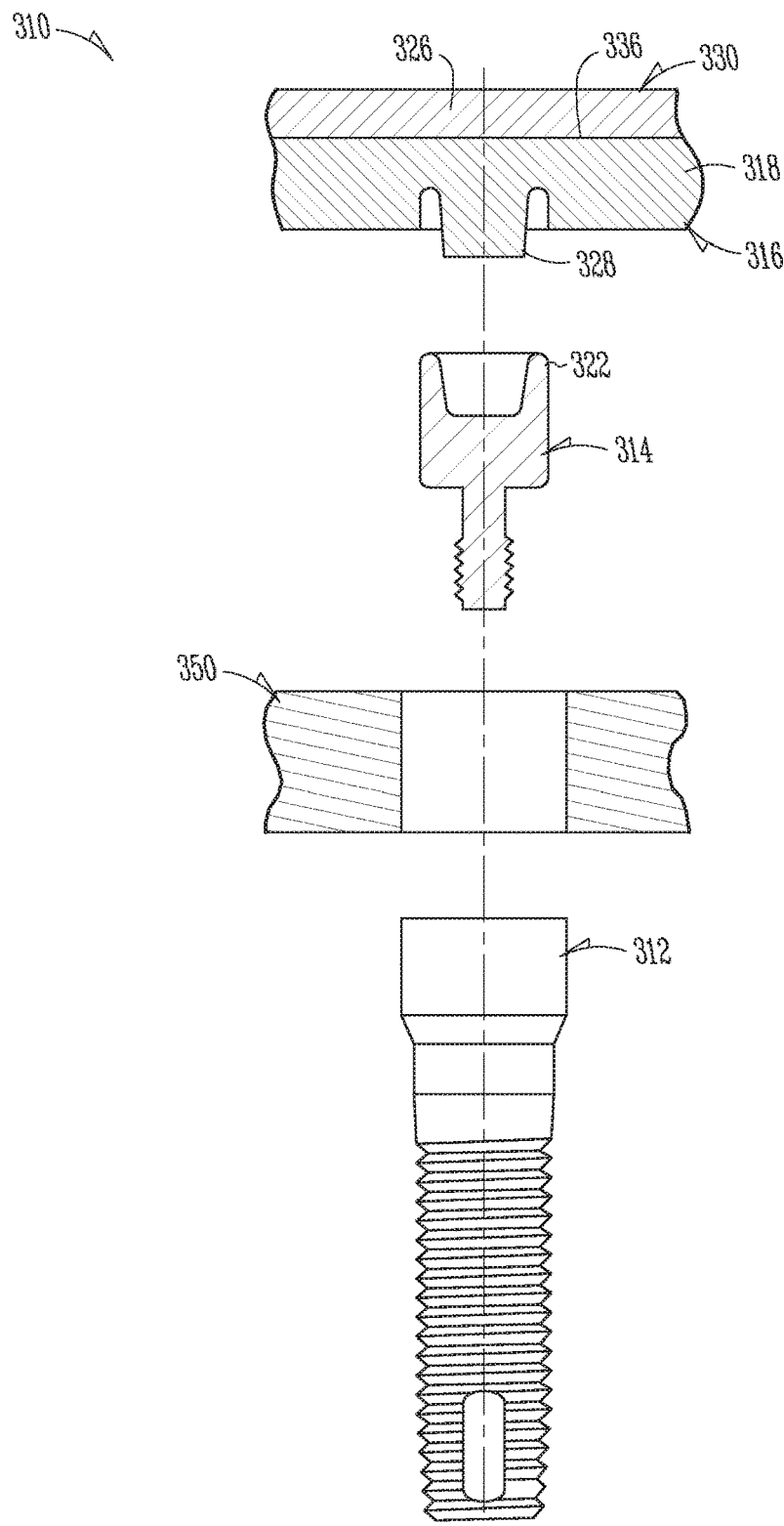
FIG. 6 is an exploded view of a dental prosthesis including an abutment and a component comprising a liner according to an example of the present disclosure.
Figure 7:
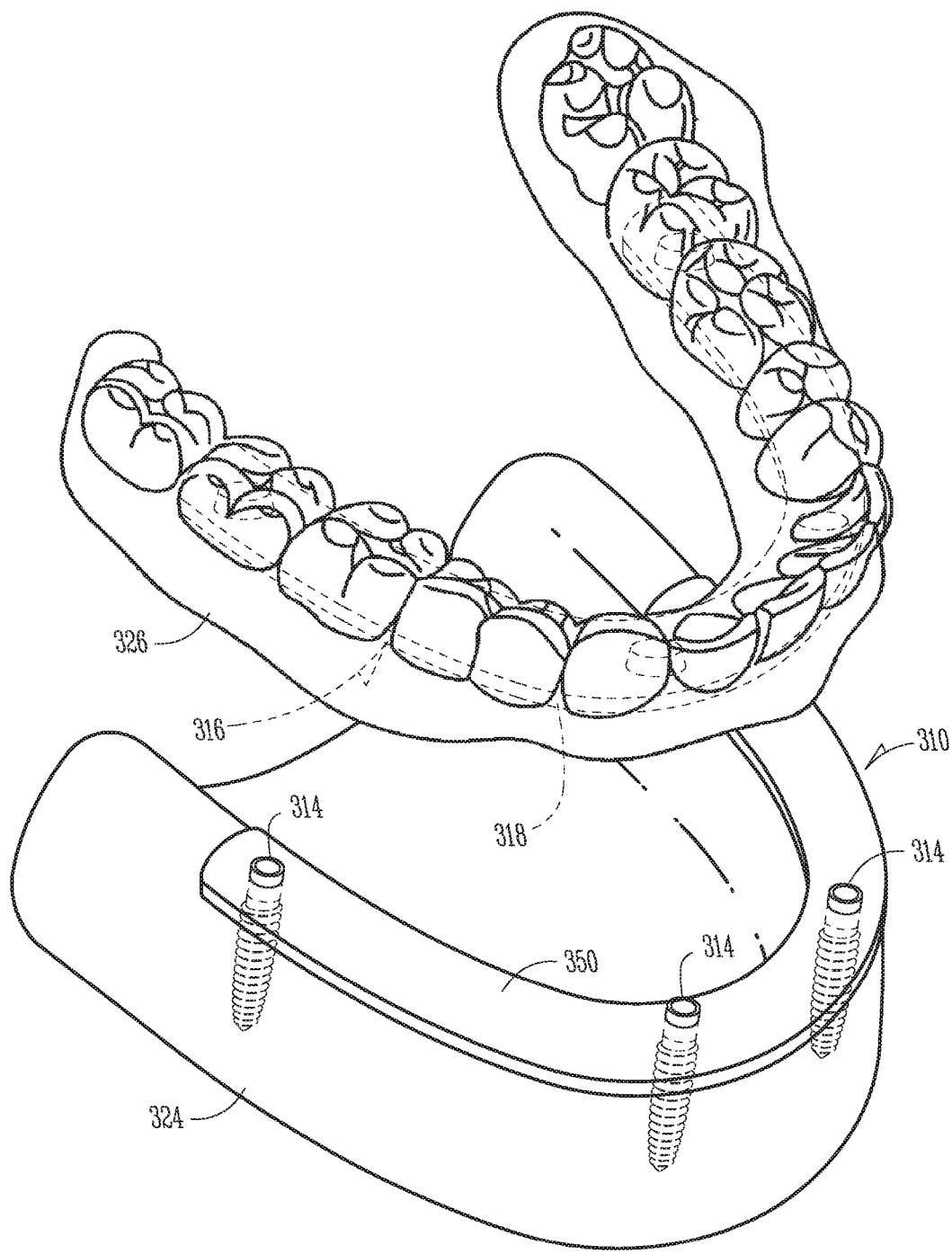
FIG. 7 is a perspective view of a plurality of dental prostheses such as those of FIG. 6 arranged in the patient's jaw and in a dental appliance according to an example of the present disclosure.

FIGS. 6 and 7 show a dental prosthesis 310 according to another example of the present disclosure. The dental prosthesis 310 can include a dental implant 312, an abutment 314, a component 316, and a bar 350. According to the example of FIGS. 6 and 7, the component 316 can comprise an insert 318, only a portion of which is shown in FIG. 6.

In FIG. 6, the dental implant 312 can be configured to couple with the abutment 314. As previously discussed, this can be accomplished by snap-fit, threads, collars, interlocking features, integrally forming the implant 312 with the abutment 314, etc. According to the example of FIG. 6, the dental implant 312 and abutment 314 can be designed to couple together through an intermediate component such as the bar 350. Only a portion of bar 350 is illustrated in FIG. 6, however, the construction of the bar 350 can be similar to that of the bar 150 of FIG. 3 and bar 250 of FIGS. 4 and 5.

FIG. 6 illustrates the abutment 314 can include a proximal end portion 322 configured as a female type connection having a rim and central recess. The component 316 (e.g., the insert 318) can be configured to couple to the abutment 314. In the example of FIG. 6, the insert 318 can include a coupling portion 328 that can be configured as a locator element to attach to the correspondingly shaped rim and central recess of the proximal end portion 322 of the abutment 314. According to some examples, the coupling arrangement can snap-fit the abutment 314 to the component 316 to couple the abutment 314 with the component 316. Although a locator type coupling arrangement is illustrated in the example of FIG. 6, in other examples other coupling configurations such as a male connection structure, a female connection structure, ball, etc. can be utilized as desired. The insert 318 can have an outer portion 336 adapted to be received in a recess 330 of the dental appliance 326 by snap-fit or other suitable connections e.g., thread, biocompatible adhesive, locking mechanism, etc.).

FIG. 7 illustrates that the dental prosthesis 310 can comprise a plurality of prostheses (e.g. two to four or more). FIG. 7 illustrates that the component 316 (e.g., insert 318) can be configured to be disposed in the dental appliance 326 (e.g., denture) while the remainder of the dental prosthesis 310 (e.g., the abutment 314, the dental implant (not shown), and the bar 350) can couple to the jaw 324. The dental prosthesis 310 can be adapted to connect the dental appliance 326 to the jaw 324. More particularly, the dental appliance 326 is adapted to overlay the jaw 324 such that each abutment 314 can interface with a. corresponding coupling portion 328 (FIG. 6) of the insert 318. The dental appliance 326 can be coupled to jaw 324 by coupling each abutment 314 to the insert 318 by, for example, snap-fitting the corresponding coupling portion 328 (FIG. 6) and the abutment 314 together.

According to the example of FIG. 7, the dental prosthesis 310 can comprise the plurality of abutments 314, the bar 350, and the insert 318. The bar 350 can be adapted to couple with the plurality of abutments 314 and can secure the plurality of abutments 314 together. The bar 350 can be configured to extend along a patent's jaw e.g., along an arch on the mandible or maxilla). The insert 318 can comprise an ultra-high molecular weight polyethylene and vitamin E and can be adapted to be disposed in a recess of the dental appliance 326. The insert 318 can be configured to couple with the plurality of abutments 314.

Although specific configurations of the dental prosthesis are shown in FIGS. 1-7 and particularly described above, other designs of dental prostheses, dental appliances, and related components that fall within the scope of the claims are anticipated. For example, the dental appliance described herein with reference to an overdenture could comprise another type of dental appliance such as a partial denture, crown, etc. according to further examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 CFR. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A dental prosthesis comprising:
an abutment adapted to be secured in a patient's jaw; and
an absorptive component comprising a first material stabilized with vitamin E, the absorptive component being configured to couple the abutment to a dental appliance, the first material having a concentration of vitamin E sufficient to provide an increased ability to absorb occlusal or shock forces borne on the dental appliance, wherein the absorptive component has a coupling portion adapted to interface with the abutment and act as an articulation surface between the absorptive component and the abutment, the abutment being configured to articulate with respect to the absorptive component by way of the articulation surface, wherein the coupling portion is composed of the first material, such that the coupling portion absorbs the occlusal or shock forces experienced between the dental appliance and the first abutment, wherein the dental appliance comprises an overdenture and the absorptive component comprises ultra-high molecular weight polyethylene and vitamin E.

2. The prosthesis of claim 1 wherein the absorptive component comprises one of a cap, a coping, a spacer, or an insert.

3. The prosthesis of claim 1, wherein the absorptive component comprises an insert, and wherein the insert is adapted to be disposed in a recess of the dental appliance and is configured to interface with the abutment and at least a second abutment.

4. The prosthesis of claim 1, wherein the absorptive component comprises a cap, and wherein the cap is adapted to be disposed in a recess of the dental appliance, the cap having the portion adapted to interface with the abutment and act as the articulation surface.

5. The prosthesis of claim 1, wherein the absorptive component comprises a spacer, and wherein the spacer is configured to couple to a metal cap that is adapted to be inserted into a recess of the dental appliance.

6. The prosthesis of claim 1, wherein the abutment includes at least one of the following coupling mechanisms:
a male connection structure;
a female connection structure;
a ball;
a spherical socket;
a locator arrangement; and
an integral bar forming a single-piece with the abutment.

7. The prosthesis of claim 1, wherein a proximal end portion of the abutment is configured to snap-fit to the absorptive component.

8. The prosthesis of claim 1, further comprising a bar configured to extend along the patent's jaw, the bar adapted to couple with the abutment and to secure the abutment to one or more additional abutments.

9. The prosthesis of claim 1, further comprising a dental implant configured to couple with the abutment and adapted for implantation in the patient's jaw.

10. The prosthesis of claim 9, wherein the dental implant has a porous metal portion of tantalum or niobium adapted to interface with a bone of the patent's jaw.

11. The prosthesis of claim 9, wherein when the dental implant is coupled to the abutment, the dental implant is fixed relative to the abutment, and wherein the abutment and the dental implant are configured to articulate with respect to the absorptive component by way of the articulation surface of the absorptive component.

12. The prosthesis of claim 1, wherein the concentration of vitamin E is about 0.01 to about 0.16 weight percent.

13. The prosthesis of claim 1, wherein the coupling portion of the absorptive component is directly coupled to the abutment, such that the articulation surface directly interfaces with the abutment.

14. A dental prosthesis comprising:
a dental appliance;
an abutment;
a dental implant configured to couple to the abutment and adapted to be implanted into the patient's jaw; and
an absorptive component comprising a first material composed of ultra-high molecular weight polyethylene stabilized with vitamin E, wherein the absorptive component is configured to be positioned between the abutment and the dental appliance, the first material including a concentration of vitamin E sufficient to provide an increased ability to absorb occlusal or shock forces between the dental appliance and the abutment, wherein the absorptive component has a coupling portion adapted to interface with the abutment and act as an articulation surface between the absorptive component and the abutment, the abutment being configured to articulate with respect to the absorptive component by way of the articulation surface, wherein the coupling portion is composed of the first material, such that the coupling portion absorbs the occlusal or shock forces experienced between the dental appliance and the abutment, wherein the dental appliance comprises an overdenture.

15. The prosthesis of claim 14, wherein a proximal end portion of the abutment is configured to snap-fit to the absorptive component.

16. The prosthesis of claim 14, wherein the concentration of vitamin E is about 0.01 to about 0.16 weight percent.

17. The prosthesis of claim 14, wherein when the dental implant is coupled to the abutment, the dental implant is fixed relative to the abutment, and wherein the abutment and the dental implant are configured to articulate with respect to the absorptive component by way of the articulation surface of the absorptive component.

18. A dental prosthesis comprising:
a plurality of abutments;
a bar adapted to couple with the plurality of abutments and secure the plurality of abutments together, the bar configured to extend along a patent's jaw;
a plurality of spacers each comprising a first material composed of ultra-high molecular weight polyethylene and vitamin E, each spacer configured to couple to one of the plurality of abutments; and
a plurality of associated metal caps each adapted to couple with a dental appliance and each configured to couple with one of the plurality of spacers, the first material of each of the plurality of spacers including a concentration of vitamin E sufficient to provide an increased ability to absorb occlusal or shock forces experienced between each of the plurality of spacers and associated one of the metal caps, when coupled together, wherein each of the plurality of spacers has a coupling portion adapted to interface with a respective one of the plurality of abutments and act as an articulation surface between the spacer and the respective one of the plurality of abutments, the respective one of the plurality of abutments being configured to articulate relative to the one of the plurality of spacers by way of the articulation surface, wherein the coupling portion of each of the plurality of spacers is composed of the first material, such that the coupling portion absorbs the occlusal or shock forces experienced between each of the plurality of spacers and associated one of the metal caps, wherein the dental appliance comprises an overdenture.

19. The prosthesis of claim 18, wherein a proximal end portion of each spacer is configured to snap-fit to one of the plurality of metal caps.

20. The prosthesis of claim 18, wherein the plurality of abutments are integral with the bar.

21. The prosthesis of claim 18, wherein the concentration of vitamin E is about 0.01 to about 0.16 weight percent.

22. A dental prosthesis comprising:
a plurality of abutments;
a bar adapted to couple with the plurality of abutments and secure the plurality of abutments together, the bar configured to extend along a patent's jaw; and
an absorptive component comprising a first material composed of ultra-high molecular weight polyethylene and vitamin E, the absorptive component configured to couple with a dental appliance and at least a first of the plurality of abutments, the first material including a concentration of vitamin E sufficient to provide an increased ability to absorb occlusal or shock forces experienced between the dental appliance and the first abutment, wherein the absorptive component has a coupling portion adapted to interface with the first abutment and act as an articulation surface between the absorptive component and the first abutment, the first abutment being configured to articulate with respect to the absorptive component by way of the articulation surface, wherein the coupling portion is composed of the first material, such that the coupling portion absorbs the occlusal or shock forces experienced between the dental appliance and the first abutment, wherein the dental appliance comprises an overdenture.

23. The prosthesis of claim 22, wherein a proximal end portion of each abutment is configured to snap-fit to the absorptive component.

24. The prosthesis of claim 22, wherein the plurality of abutments are integral with the bar.

25. The prosthesis of claim 22, wherein the concentration of vitamin E is about 0.01 to about 0.16 weight percent.

* * * * *